(12) United States Patent
Bettmann et al.

(10) Patent No.: US 10,073,073 B2
(45) Date of Patent: Sep. 11, 2018

(54) APPARATUS FOR DETERMINING CONTENT OF AT LEAST ONE OXIDIZABLE CONSTITUENT OF AN AQUEOUS SAMPLE

(75) Inventors: Oliver Bettmann, Russelsheim (DE); Ulrich Kathe, Leonberg (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 91 days.

(21) Appl. No.: 12/994,038

(22) PCT Filed: May 25, 2009

(86) PCT No.: PCT/EP2009/056258
§ 371 (c)(1),
(2), (4) Date: Nov. 22, 2010

(87) PCT Pub. No.: WO2009/144178
PCT Pub. Date: Dec. 3, 2009

(65) Prior Publication Data
US 2011/0076198 A1    Mar. 31, 2011

(30) Foreign Application Priority Data
May 29, 2008    (DE) .................. 10 2008 025 877

(51) Int. Cl.
*G01N 33/18* (2006.01)
*G01N 33/00* (2006.01)

(52) U.S. Cl.
CPC ..... *G01N 33/1846* (2013.01); *G01N 33/0014* (2013.01)

(58) Field of Classification Search
CPC . G01N 31/12; G01N 33/0014; G01N 33/1846
(Continued)

(56) References Cited

U.S. PATENT DOCUMENTS 3,172,732 A    3/1965    Hines et al.
3,296,435 A *   1/1967    Teal et al. ................. 436/146
(Continued)

FOREIGN PATENT DOCUMENTS

DE    1 598 492    7/1970
DE    44 17 247    11/1995
(Continued)

OTHER PUBLICATIONS

German Search Report dated Oct. 5, 2011.

*Primary Examiner* — Lyle Alexander
*Assistant Examiner* — Bryan Kilpatrick
(74) *Attorney, Agent, or Firm* — Christopher R. Powers; PatServe

(57) ABSTRACT

An apparatus for determining the content of at least one oxidizable constituent of an aqueous, liquid sample, comprising a high temperature reactor for decomposing the liquid sample and forming a gaseous mixture, which contains at least the constituent as a gaseous oxide, wherein the high temperature reactor has a liquid inlet for delivery of the liquid sample and a gas inlet for delivery of a carrier gas, and is connected via a gas discharge with an analysis chamber, wherein a condensing unit is placed in front of the analysis chamber for condensing water from the gas mixture, wherein, during operation of the apparatus, a gas stream of the carrier gas with the gas mixture of the high temperature reactor passes via the gas discharge and the condensing unit into the analysis chamber, and wherein, between the gas discharge and the condensing unit, a heatable filter unit is interposed for removal of salts and/or metal oxides from the gas mixture, and the gas discharge, the filter unit and optionally connecting elements arranged between gas discharge and filter unit are thermally insulated and/or equipped with heating elements in such a manner that their (Continued)

temperature during operation of the apparatus is settable to more than 100° C.

22 Claims, 1 Drawing Sheet

(58) Field of Classification Search
USPC ......... 422/78, 129; 436/155, 160; 250/341.6
See application file for complete search history.

(56) References Cited

U.S. PATENT DOCUMENTS

| | | | |
|---|---|---|---|
| 3,410,662 A | 11/1968 | Murphy | |
| 4,133,762 A * | 1/1979 | Visceglia | B01D 15/00 |
| | | | 210/186 |
| 4,272,481 A | 6/1981 | Ahlstrom, Jr. et al. | |
| 4,582,686 A | 4/1986 | Tsuji | |
| 6,475,802 B2 * | 11/2002 | Schaedlich et al. | 436/81 |
| 6,932,951 B1 * | 8/2005 | Losey et al. | 422/211 |
| 2004/0179980 A1 * | 9/2004 | Pattekar et al. | 422/130 |
| 2012/0028361 A1 * | 2/2012 | Kathe et al. | 436/50 |

FOREIGN PATENT DOCUMENTS

| | | |
|---|---|---|
| DE | 44 17 247 A | 11/1995 |
| EP | 0 964 248 | 12/1999 |
| EP | 0 964 248 A1 | 12/1999 |
| JP | 20000 65696 A | 3/2000 |
| JP | 2000065696 | 3/2000 |
| JP | 2007 054791 A | 3/2007 |
| JP | 2007054791 | 3/2007 |

* cited by examiner

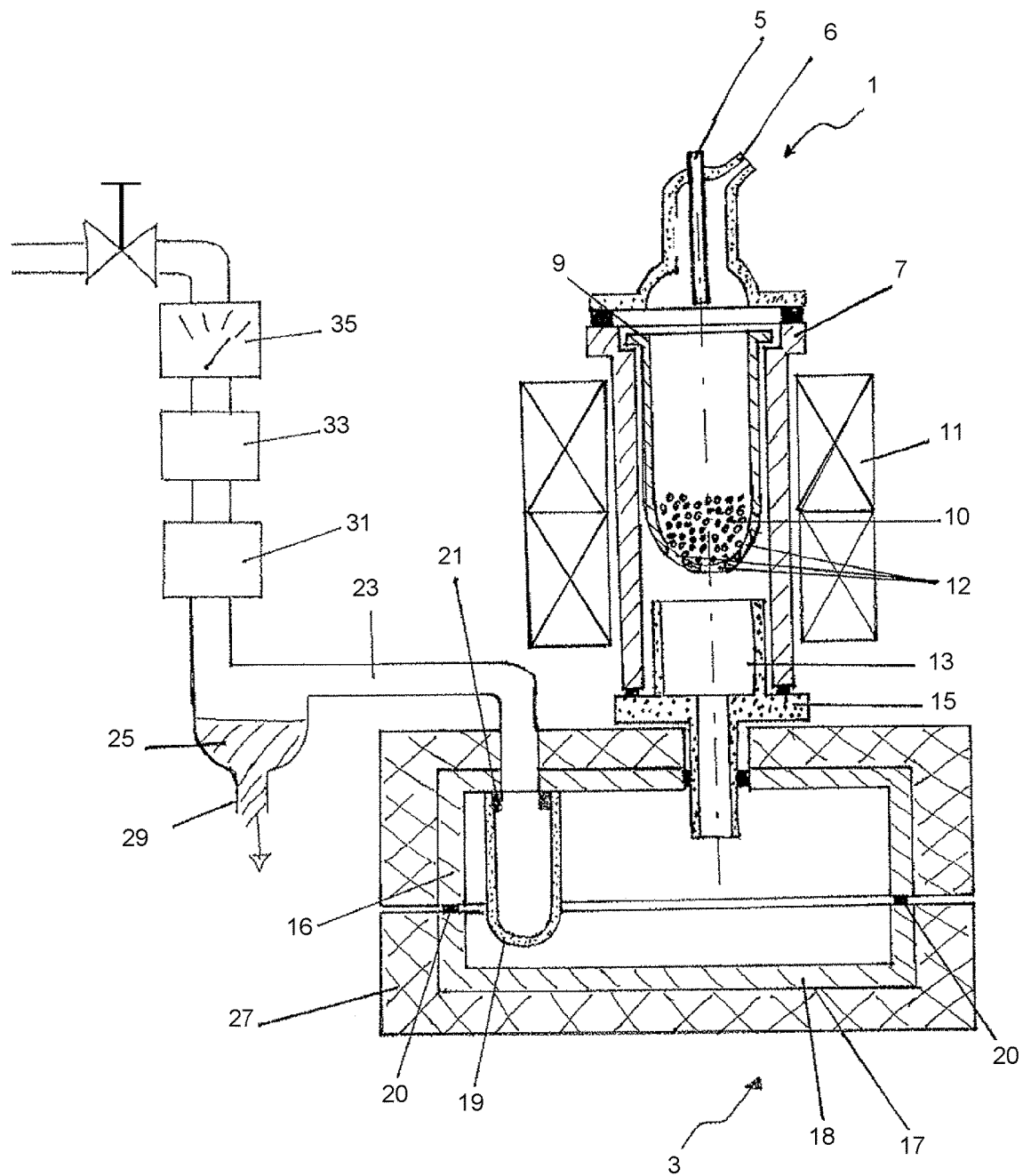

APPARATUS FOR DETERMINING CONTENT OF AT LEAST ONE OXIDIZABLE CONSTITUENT OF AN AQUEOUS SAMPLE

TECHNICAL FIELD

The present invention relates to an apparatus for determining the content of at least one oxidizable constituent of an aqueous, liquid sample, wherein the apparatus comprises a high temperature reactor for decomposing the liquid sample and forming a gaseous mixture, which contains at least the constituent as a gaseous oxide.

BACKGROUND DISCUSSION

Such apparatuses are applied, for example, for determining the carbon content and/or the nitrogen content of wastewater. Some of the most important constituents to be determined in waste waters are the following:

TC (Total Carbon, total carbon content), the entire amount of carbon contained in the aqueous liquid;

TOC (Total Organic Carbon, total organically bound carbon), the entire amount of carbon contained in the form of organic compounds in the aqueous liquid;

TIC (Total Inorganic Carbon, total inorganically bound carbon), the entire amount of carbon contained in the form of inorganic compounds in the aqueous liquid;

$TN_b$, (Total Nitrogen, total bound nitrogen), the entire amount of bound nitrogen contained in the aqueous liquid.

In the case of known methods, a liquid sample of small volume of, for example, a few 100 µl is fed to the high temperature reactor. In determining TOC, there occurs, in given cases, a pretreating for removing the inorganic compounds, e.g. by acidification, wherein carbon dioxide ($CO_2$) is given off and removed by purging. In the high temperature reactor, the organic constituents are thermally decomposed to $CO_2$, and the nitrogen containing constituents to nitrogen oxides $NO_x$. The acronym $NO_x$ represents a mixture of nitrogen oxides of different degrees of oxidation, which has, however, NO as the main component, namely at about 98%. In a smaller amount, the mixture also contains $NO_2$; however, conversion of the NO into $NO_2$ under the given conditions takes a relatively long time. In the decomposition in the high temperature reactor, there arises a gas mixture, which contains, besides $CO_2$ and $NO_x$, gaseous $H_2O$, as well as impurities, for example, in the form of sublimated salts or metal oxides. The gas mixture is transported with the assistance of a carrier gas (which, as a rule, also delivers the oxygen needed for reaction) through a cooler with water separator, a gas filter and an analytical unit. The amount of the arising $CO_2$, or $NO_x$, is ascertained, for example, by infrared or chemiluminescent measurement, and, from this value, the TOC or $TN_b$ is calculated.

For liquid samples, the reaction temperature is usually about in the range of 680° C. to 1000° C., wherein higher temperatures, in principle, favor the sample decomposition. Complete conversion of the carbon, or nitrogen, compounds contained in the sample is supported through the use of catalysts, for example, platinum, or oxygen transferees, e.g. ceroxide or nickel oxide. It is also possible to perform the decomposition of the sample without catalyst or oxygen transferer. In this case, the reaction is, as a rule, performed at temperatures of more than 1000° C.

Contained in the liquid samples and therewith also correspondingly in the gas mixture occurring in the high temperature reactor are frequently matrix components, such as: Salts, e.g. chloride, sulfates or phosphates, which, at the temperatures reigning in the reaction zone of the high temperature reactor, transfer by sublimation into the gas phase; metal oxides, which can be present as solid particles within the gas mixture; and acids or basic components. These matrix components can disturb or even corrupt the determining of the oxidizable constituents. For example, in cold regions of the apparatus, desublimated salts and metal oxide particles can separate from the gas mixture and lead to the clogging of narrow gas lines or filters. Moreover, corrosive gases, vapors or aerosols can arise from the salts or other components in the gas phase, and be distributed by the carrier gas into the regions of the apparatus, through which the carrier gas flows. In this way, sensitive parts of the apparatus, especially the detectors present for the analysis, can be damaged.

Measures are known from the state of the art for reducing these damaging effects of the matrix components, especially the salts.

Thus, DE 44 17 247 B4 discloses an analytical apparatus having a combustion furnace for liquid samples for determining the content of oxidizable constituents, in which an insert is arranged, which contains filler elements of quartz glass or ceramic material. The insert is arranged in a region of the combustion furnace, in which the operating temperature lies between 100° C. and 400° C. At these temperatures, the salts present in the gas mixture deposit on the filler elements and, therefore, do not get into the remaining regions of the analytical apparatus.

From time to time, the insert must, however, be replaced or deinstalled and cleaned, since its ability to catch the precipitated salts is limited. This requires a complex sealing technology, especially since the sealing surfaces at the position of the insert in the combustion furnace must be designed for high temperatures. During the replacement of the insert, the combustion furnace must be cooled down, which leads to a down time of the analytical apparatus. When taking out the insert to be replaced or regenerated, there is a danger that salt particles can fall out of the insert and foul the apparatus. Especially damaging is the situation, when the salt particles reach the sealing surfaces, since then a reliable sealing in the case of renewed start-up is no longer assured.

In U.S. Pat. No. 4,078,894, an apparatus for waste water analysis with a high temperature reactor is shown, in which a liquid sample is converted to a gas mixture by heating in the presence of a carrier gas acting as oxidizing agent. The gas discharge of the reactor opens into a chamber, which is filled in a lower region with water, and in which the gas mixture is so greatly cooled off, that therein contained salts fall out and are dissolved in the water. By pumping the water from the chamber, the salts are removed from the system. Interaction of the condensate with the high velocity gas stream flowing past can, however, lead to the formation of damaging aerosols in the case of such an apparatus.

In JP 2007-054791 A, an apparatus to treatment of wastewater by means of burning is shown, to which is connectable an analytical device for determining various constituents in the process off-gas. In order not to corrupt the measuring, it is necessary that, before introduction of the process off-gas into the analytical device, salt containing fog, or aerosols be removed from the process off-gas. This occurs by means of a gas cleaning unit (scrubber) with, connected in series, a fine filter, which are arranged together in a housing. The housing is heated to a temperature above the condensation temperature of the water content in the process off-gas and below 150° C., in order to avoid condensing of water from the process off-gas. The removal of aerosols from an apparatus is, however, associated with relatively high apparatus complexity.

SUMMARY OF THE INVENTION

An object of the invention is to provide an apparatus for determining the content of at least one oxidizable constituent of an aqueous, liquid sample, which overcomes the disadvantages of the apparatuses known from the state of the art. Especially, it is an object of the invention to provide such an apparatus having a simple to maintain, especially easily exchangeable, filter apparatus, which permits a fast and comprehensive removal of salts from the gas mixture while preventing aerosol formation, as well as the removal of other disturbing components, such as e.g. metal oxides, possibly present in the gas mixture.

This object is achieved by an apparatus for determining the content of at least one oxidizable constituent of an aqueous, liquid sample, wherein the apparatus comprises a high temperature reactor for decomposing the liquid sample and forming a gaseous mixture, which contains at least the constituent as a gaseous oxide,
wherein the high temperature reactor has a liquid inlet for delivery of the liquid sample and a gas inlet for delivery of a carrier gas, and
is connected via a gas discharge with an analysis chamber,
wherein a condensing unit is placed in front of the analysis chamber for condensing water from the gas mixture,
wherein, during operation of the apparatus, a gas stream of the carrier gas with the gas mixture of the high temperature reactor passes via the gas discharge and the condensing unit into the analysis chamber,
wherein, between the gas discharge and the condensing unit, a filter unit is interposed for removal of salts and/or metal oxides from the gas mixture, and the gas discharge, the filter unit and optionally connecting elements arranged between gas discharge and filter unit are thermally insulated and/or equipped with heating elements in such a manner, that their temperature during operation of the apparatus is settable to more than 100° C.

In the case of moving the filter unit in the apparatus of DE 44 17 247 B4 into a region cooler during operation of the apparatus in the gas flow direction behind the high temperature reactor, it is observed, that more aerosol occurs in the system. This seems to be connected therewith, that parts of the apparatus between the high temperature reactor and the filter unit cool off to temperatures below 100° C., so that water present in the gas stream condenses on them. Salts contained in the gas stream dissolve in the condensed water, partially accompanied by formation of acid. The gas stream effects a fine distribution of the so formed salt, or acid, solution as aerosol. In experiments, it could be shown, that aerosols occur in detectable amount only when there is condensation of the unfiltered gas mixture.

In the case of the here described apparatus, therefore, between the gas discharge and the condensing unit, a filter unit is arranged for the removal of salts from the gas mixture. At the same time, the filter unit also removes from the gas stream metal oxides or other particles present in the gas mixture, in given cases, for example, as solid particles. Through the arrangement of the filter unit between the gas discharge and the condensing unit, there is assured, on the one hand, an easier exchangeability and/or maintenance of the filter unit, since the temperature during operation of the apparatus in this region is already markedly smaller than in the high temperature reactor. On the other hand, in this way, already before the condensing of the water present in the gas mixture, salts and/or metal oxides are largely removed from the gas mixture.

In order to assure that no condensation occurs in the gas stream before the filter unit, it is of advantage to equip the gas discharge, the filter unit, and, in given cases, connecting elements, such as e.g. gas lines, present between the filter unit and the gas discharge, with thermal insulation and/or heating elements, so that their temperature during operation is set to more than 100° C. The concept of setting the temperature includes here, besides the active controlling of the temperature, also a maintaining of a temperature above 100° C. alone by means of thermal insulation or by uncontrolled heating.

The reaction zone reaches during operation a temperature of 600° C. up to more than 1000° C. For supporting complete conversion of the oxidizable constituents, for example, organic carbon containing or nitrogen containing compounds, optionally a catalyst, or an oxygen transferer, such as, for example, a platinum-catalyst or ceroxide or nickel oxide, is provided in the reaction zone of the high temperature reactor. The temperature of the reaction zone is then set at a value between 680° C. and 1000° C. When no catalyst or oxygen transferer is used, then the reaction zone is brought during operation, as a rule, to temperatures of more than 1000° C.

Used as carrier gas is preferably oxygen or an oxygen containing gas or gas mixture, which simultaneously serves as oxidizing agent for the constituents to be determined. The apparatus is so embodied that, during operation, a gas stream of the carrier gas (present in excess) with the gas mixture develops from the high temperature reactor via the gas outlet and the condensing unit into the analysis chamber.

The liquid inlet and the gas inlet are, in each case, embodied as supply lines on the input side of the high temperature reactor. Liquid, and gas, inlet can also be implemented by a single supply line. In this case, the carrier gas is metered together with the liquid sample into the high temperature reactor.

In an advantageous embodiment, the filter unit comprises a first region, which is embodied to remove salts and/or metal oxides from the gas mixture by desublimation and/or sedimentation and, connected after the first region, i.e. arranged in the direction of the gas stream behind the first region, a second region, which is embodied to remove salts and/or metal oxides from the gas mixture through retention in a filter means.

The term, sedimentation, means the settling of particles from the gas mixture under the influence of forces, especially the farce of gravity. Reigning in a region located near the gas discharge of the high temperature reactor, in the gas discharge itself, in connecting elements present, in given cases, between gas discharge and filter unit, as well as within the filter unit are clearly lower temperatures than in the reaction zone of the high temperature reactor. There, salts contained in the gas stream can desublimate and deposit as solid salt particles. Under the influence of the force of gravity, in given cases, supported by lessening the flow velocity, at the entry of the gas stream into the filter unit, these salt particles, in given cases, together with other solid particles, e.g. metal oxide particles, present in the gas stream in the filter unit can deposit. The first region of the filter unit is embodied in such a manner, that the desublimated and settled salt as well as settled metal oxide particles are, at least for the most part, retained there.

In order to avoid that the gas stream to the analysis chamber in the first region of the filter unit stirs up deposited particles and further transports them in the direction of the analysis chamber, a second region of the filter unit is embodied, to hold back particles with a filter means.

In a further development, the filter unit is heatable by means of at least one heating element to an operating temperature above the condensation temperature of water, especially to a temperature between 100° C. and 150° C., preferably between 110° C. and 130° C. In this way, condensation of water is avoided within the filter unit.

In a further development, the gas discharge and the filter unit are connected with one another via a thermally insulated and/or heated gas line as connecting element.

In an advantageous further development, the gas discharge and/or the gas line, via which the gas discharge is connected with the filter unit, have a large inner diameter, especially a diameter of more than 3 mm, and are formed in such a manner, that salts or other particles solid in the high temperature reactor in the region of the gas discharge get into the filter unit, especially into the first region of the filter unit, at least partially due to the effect of gravitation and/or with the gas stream. In this way, the force of gravity is advantageously utilized, in order to transport solid particles into the filter unit. At the same time, in this way, a clogging of the gas discharge, or a blocking of the gas stream by accumulating particles is prevented.

In a further development, the filter unit includes in the first region a filter chamber hermetically sealed relative to the environment for collecting desublimated and/or sedimented salt and/or sedimented metal oxide.

In an embodiment, the filter chamber is essentially formed by a lid, connected releasably, especially via a quick coupler, with the gas discharge or the gas line from the gas discharge to the filter unit, and a pot connected releasably with the lid. This has the advantage that the filter unit can be released and removed from the apparatus rapidly and simply for maintenance or for replacement. In case the maintenance only requires emptying the filter chamber, the lid can remain connected with the gas discharge and only the pot removed and emptied.

In an embodiment, the filter unit includes in the second region a fine filter, which gas permeably seals the filter unit, especially the interior of the filter chamber, relative to the condensing unit. The fine filter is preferably secured to a holder connected with the lid. This has the advantage that only the filter chamber or even only the pot need be released also for the replacement of the fine filter.

In an advantageous further development, the fine filter includes a filter means having a structure, which is embodied in such a manner that the separation of the salts or other substances contained in the gas stream occurs according to the principle of deep filtration, in the interior of the filter means. In deep filtration, the filter means comprises individual particles or a porous structure, wherein the retained materials are mainly adsorbed within the filter means, i.e. in the pore structure or on the particle surfaces. This has relative to the principle of cake, or surface, filtration, in the case of which the retained constituent deposits on the surface of the filter means as cohesive filter cake, the advantage, that a clogging of the fine filter occurs more slowly and, thus, the time intervals between maintenance can be lengthened.

For example, the fine filter comprises a PTFE-sinter, filter element, an active charcoal filter element, PP discontinuous fibers or a stainless steel mat, wherein the average pore size of the fine filter amounts to 0.4 to 100 μm, especially 5 to 25 μm.

In an advantageous embodiment, a pressure sensor is arranged upstream from the fine filter, especially within the gas inlet for delivery of the carrier gas. The pressure sensor enables monitoring of the pressure before the filter unit. A pressure rise indicates a clogging of the fine filter. With the pressure measurement, in the case of the exceeding of a predetermined pressure threshold value, a warning signal can be output, for indicating need for filter maintenance.

BRIEF DESCRIPTION OF THE DRAWINGS

The invention will now be explained on the basis of an example of an embodiment illustrated in the drawing, the sole figure of which shows as follows:

FIG. 1 is a schematic representation of an apparatus (with filter unit) for determining the content of at least one oxidizable constituent of an aqueous, liquid sample.

DETAILED DISCUSSION IN CONJUNCTION WITH THE DRAWING

In the case of the apparatus 1 illustrated in FIG. 1, the liquid sample to be examined, for example, a wastewater sample, is fed via an injection nozzle 5 to a high temperature reactor, for example, in the form of a pyrolysis tube 7. At the same time, the high temperature reactor is fed via another supply line 6 an oxygen containing, carrier gas. The pyrolysis tube 7 contains an insert 9, which contains a catalyst 10, which supports the reaction of the liquid sample with the oxygen containing, carrier gas. The temperature of the high temperature reactor is adjustable by means of a heating apparatus 11 surrounding the pyrolysis tube 7. In the region of the insert 9 is located the reaction zone, in which during operation a temperature between 680° C. and 1000° C. reigns. Optional, besides the catalyst 10, there can be accommodated in the insert 9 within the reaction zone additional bulk material (not shown), which is retained by the sieve floor of the insert 9 provided with passageways 12. In the contact with the catalyst 10 and the bulk material, the liquid sample heats rapidly to reaction temperature and is transferred into the gas phase, so that no liquid passes through the sieve floor into the remaining parts of the apparatus 1. Beneath the insert 9 within the pyrolysis tube 7 there is arranged another chamber 13, in which during operation already a lower temperature reigns than in the reaction zone.

At the lower end of the pyrolysis tube 7 vertically directed during operation of the apparatus 1, opposite the injection nozzle 5, is located a gas outlet 15, which opens into the interior of the filter chamber 17 of a filter unit 3 directly connected with the gas outlet 15, so that a gas mixture produced in the pyrolysis tube 7 can flow, via the passageways 12, the chamber 13 and the gas outlet 15, with the carrier gas, into the interior of the filter chamber 17. The filter chamber 17 is essentially formed by a lid 16 and a pot 18. The lid 16 is connected via a quick coupler (not shown) releasably with the gas outlet 15 of the high temperature reactor. The pot 18 is, in turn, connected releasably with the lid 16, however, sealed by means of the seals 20 hermetically relative to the environment.

Filter chamber 17 is connected with a condensing unit 25 via a gas line 23. A cylindrical fine filter 19 seals the interior of the filter chamber 17 gas permeably relative to the gas line 23. The fine filter 19 is connected with the lid 16 releasably via a holder 21. The filter chamber 17 and the gas outlet 15 of the high temperature reactor are surrounded by an insulating jacket 27 of insulating material, such as, for example, temperature resistant, foam material. Optional, the gas outlet 15 and the filter chamber 17 can be provided with heating elements (not shown). These can be arranged, for example, outside of the filter chamber 17, between the outer wall of the filter chamber 17 and the insulating jacket 27. For example, a heating foil adhered externally on the filter chamber 17 can be used as heating element.

A gas stream flowing from the gas outlet 15 into the interior of the filter chamber 17, which essentially is composed of the gas mixture arising in the high temperature reactor and the carrier gas, can flow via the filter chamber 17, after passing the fine filter 19, through the gas line 23 into the condensing unit 25. The condensing unit 25 serves for the separation of water from the gas stream and is, therefore, in given cases, provided with a cooler, in order to accelerate condensation from the gas stream. The condensate is removed from the apparatus 1 via a line 29.

Arranged in flow direction of the gas stream behind the condensing unit 25 are an optional drying unit 31, a further filter 33 and an analysis chamber 35. In the analysis chamber 35, the content of gaseous $CO_2$ and/or $NO_x$ is ascertained. As a rule, for determining $CO_2$ content, an infrared measuring arrangement is used, e.g. an infrared detector. For determining the $NO_x$ content, as a rule, a chemiluminescence detector is applied. The measurement signals are fed to a data processing unit (not shown), which delivers processed signals to a display and/or recording unit (likewise not shown).

The apparatus 1 is sealed hermetically relative to the environment along the total flow path of the gas stream, so that no gas can escape from the apparatus 1.

At the temperatures reigning in the reaction zone, salts, such as chlorides, sulfates or phosphates, contained in the liquid sample provided in the high temperature reactor transfer by sublimation into the gas phase. However, in a region of the pyrolysis tube 7 in the vicinity of the gas outlet 15, for the example in the chamber 13, there rules, already, a lower temperature of 150-450° C., in the case of which at least a part of the salts already transfers back by desublimation into the solid phase and deposits in the form of salt particles on the tube, or pipe, wall or in the gas outlet 15. With increasing distance from the reaction zone of the high temperature reactor, the temperature falls during operation still further. Correspondingly, the gas outlet 15 and the filter unit 3 possess during operation a still lower temperature, so that desublimation of the salts in the gas phase from the gas stream is amplified in these regions. A deposition of salt particles can thus occur in the region of the pyrolysis tube 7 located in the vicinity of the gas outlet 15, in the chamber 13, in the gas outlet 15 and in the filter unit 3.

The gas outlet 15 of the high temperature reactor is embodied to have a large inner diameter, i.e. it possesses an inner diameter of more than 3 mm. In this way, salt particles deposited in the pyrolysis tube 7 or in the gas outlet 15 fall through the gas outlet 15 into the filter chamber 17, without the danger of a clogging of the gas outlet 15. It is supplementary of advantage so to configured the gas outlet 15 that these salt particles reach the filter chamber 17 at least partially due to the gravitational effect. In this regard, for example, the interior of the tubular gas outlet 15 can be so formed, that there is within the tube at least one path, which falls strongly monotonically in the direction of the filter chamber 17. The transport of the salt particles into the filter chamber 17 is not only promoted by the force of gravity, but, instead also by the gas flow, which entrains the salt particles and transports them into the filter chamber 17. Advantageously, the diameter of the gas outlet 15 lies in the range between 6 and 12 mm; in principle, it can, however, also be selected to be exactly as large as the diameter of the pyrolysis tube 7.

Salt particles falling through the gas outlet 15 and deposited in the filter chamber 17 collect in the interior of the filter chamber 17. This is supplementary favored by the fact that, in the flow direction behind the gas outlet 15, the gas path becomes wider upon entry into the interior of the filter chamber 17 wide and, as a result, the gas flow velocity sinks. The reduced flow velocity facilitates the settling of solid particles contained in the gas stream. The filter chamber 17 forms thus both a collector for salt particles removed from the gas stream by sedimentation (settling), as well as also for salt particles, which are formed in the interior of the filter chamber 17 through desublimation. In the same way as for salt particles, also other solid particles present, in given cases, in the gas stream, as for example metal oxide particles, are transported into the interior of the filter chamber and removed from the gas stream by sedimentation.

In the direction to the analysis chamber 35, the gas stream passed through the fine filter 19. This serves for retaining salt particles still contained in the gas stream and not deposited or stirred up in the filter chamber by the gas stream. The fine filter 19 includes as filter means, for example, a PTFE sinter filter element, an active charcoal filter element, PP discontinuous fibers or a stainless steel mat, wherein the average pore size of the filter means amounts to 0.4 to 100 μm, preferably 5 to 25 μm. The operation of the filter means is characterized by the fact that the particles are bound and retained mainly in the interior of the pore structure of the filter means.

In order to maintain the filter unit 3, either the entire filter unit is separated at the quick couplers from the gas outlet 15 and the gas line 23, the filter chamber 17 emptied and the fine filter 19 regenerated or replaced. Alternatively, also only the pot 18 can be taken off and emptied. After taking off the pot 18, also the fine filter 19 is freely accessible and can be released from the holder 21, in order to replace or regenerate it. For monitoring the filter unit 3, in principle, a pressure sensor can be provided at any position in the apparatus upstream from the fine filter. Advantageously, the pressure sensor is provided in the supply line 6 for the transport gas for the high temperature reactor, since in this region temperatures are still low. Alternatively, the pressure sensor can, however, also be provided in the region of the gas outlet 15 or in the filter unit 3. If the pressure sensor detects a pressure rise, such is an indication of a clogging of the fine filter 19, which the gas stream can then no longer pass through unimpeded. If the pressure rises above a fixed threshold value, a data processing and/or output unit connected with the pressure sensor can output an alarm, which indicates need for maintenance of the filter unit 3.

For preventing the occurrence of aerosols, it is of advantage, as already explained above, when, before separation of the salts, there is no condensation of water from the gas mixture formed in the high temperature reactor from the liquid sample. In order to assure this, the entire region, through which the gas stream flows between the reaction zone in the insert 9 up to and including the filter unit 3, is insulated by means of an insulating jacket 17 thermally relative to the environment. In operation, the temperature of the filter unit 3 as well as all regions of the apparatus 1, through which the gas stream flows between the high temperature reactor and the filter unit 3, are controlled to a temperature above 100° C.

The invention claimed is:

1. An apparatus for determining the content of at least one oxidizable constituent of an aqueous, liquid sample, comprising:
a high temperature reactor for decomposing the liquid sample and forming a gaseous mixture, which contains at least the constituent as a gaseous oxide, said high temperature reactor settable to a reactor temperature and including a liquid inlet for delivery of the liquid sample, a gas inlet for delivery of a carrier gas, and a gas outlet;
a condensing unit for condensing water from the gas mixture; and
an analysis chamber,
wherein the high temperature reactor, the condensing unit and the analysis chamber are arranged sequentially in a fluid communication path, so that during operation of the apparatus, a gas stream of the carrier gas and the gas mixture passes from the high temperature reactor via said gas outlet, through said condensing unit and into said analysis chamber,
wherein a heatable filter unit is interposed in said fluid communication path between said high temperature reactor and said condensing unit, for removal of salts and/or metal oxides from the gas stream passing from said gas outlet to said condensing unit, the filter unit arranged separate from the high temperature reactor such that the filter unit is replaceable and settable to a filter temperature substantially below the reactor temperature, and
wherein said gas outlet and said heatable filter unit are thermally insulated and/or equipped with heating elements such that during operation of the apparatus the filter temperature and a gas outlet temperature are settable to less than the reactor temperature and between 100° C. and 150° C.

2. The apparatus as claimed in claim 1, wherein:
said filter unit comprises a first region including the filter chamber, which is embodied to remove salts and/or metal oxides from the gas mixture by desublimation and/or sedimentation and, connected in the direction of the gas stream behind the first region, a second region, which is embodied to remove salts and/or metal oxides from the gas mixture by retention in a filter means.

3. The apparatus as claimed in claim 1, wherein:
said heatable filter unit is heatable by means of at least one heating element to an operating temperature above the condensation temperature of water.

4. The apparatus as claimed in claim 2, wherein:
said gas outlet has a diameter of more than 3 mm, and is formed such that salts and/or metal oxides deposited in the high temperature reactor in the region of said gas outlet get into said heatable filter unit, at least partially due to the effect of gravitation and/or with the gas stream.

5. The apparatus as claimed in claim 2, wherein:
said filter chamber is hermetically sealed relative to the environment for collecting desublimated and/or sedimented salt and/or sedimented metal oxide.

6. The apparatus as claimed in claim 5, wherein:
said filter chamber is formed essentially of a lid releasably connected with said gas outlet, and a pot connected releasably with said lid.

7. The apparatus as claimed in claim 2, wherein:
said heatable filter unit comprises in the second region a fine filter, which seals said heatable filter unit gas permeably relative to said condensing unit.

8. The apparatus as claimed in claim 7, wherein:
said fine filter comprises a filter means having a structure, which is embodied in such a manner that separation of salts and/or metal oxides occurs according to the principle of deep filtration in the interior of the filter means.

9. The apparatus as claimed in claim 7, wherein:
said fine filter comprises a PTFE sinter filter element, an active charcoal filter element, PP discontinuous fibers or a stainless steel mat; and
the average pore size of said fine filter amounts to 0.4 to 100 μm.

10. The apparatus as claimed in claim 7, further comprising:
a pressure sensor arranged upstream from said fine filter.

11. The apparatus as claimed in claim 4, wherein:
said gas outlet is formed in such a manner that salts and/or metal oxides deposited in the high temperature reactor in the region of said gas outlet get into the first region of said heatable filter unit, at least partially due to the effect of gravitation and/or with the gas stream.

12. The apparatus as claimed in claim 6, wherein:
said lid is releasably connected with said gas outlet via a quick coupler.

13. The apparatus as claimed in claim 10, wherein:
said pressure sensor is arranged within said gas inlet for delivery of the carrier gas.

14. An apparatus for determining the content of at least one oxidizable constituent of an aqueous, liquid sample, comprising:
a high temperature reactor for decomposing the liquid sample and forming a gaseous mixture, which contains at least the constituent as a gaseous oxide, said high temperature reactor settable to a reactor temperature and including a liquid inlet for delivery of the liquid sample, a gas inlet for delivery of a carrier gas, and a gas outlet;
a condensing unit for condensing water from the gas mixture; and
an analysis chamber, wherein:
the high temperature reactor, the condensing unit and the analysis chamber are arranged sequentially in a fluid communication path, so that during operation of the apparatus, a gas stream of the carrier gas and the gas mixture pass from the high temperature reactor via said gas outlet, through said condensing unit and into said analysis chamber,
a heatable filter unit is interposed in said fluid communication path between said high temperature reactor and said condensing unit, for removal of salts and/or metal oxides from the gas stream, the filter unit arranged separate from the high temperature reactor such that the filter unit is settable to a filter temperature substantially below the reactor temperature,
said gas outlet and said heatable filter unit are thermally insulated and/or equipped with heating elements such that during operation of the apparatus the filter temperature and a gas outlet temperature are settable to more than 100° C. but less than the reactor temperature, and
said filter unit comprises a first region, which is embodied to remove salts and/or metal oxides from the gas mixture by desublimation and/or sedimentation and, connected in the direction of the gas stream behind the first region, a second region, which is embodied to remove salts and/or metal oxides from the gas mixture by retention in a filter means, said filter unit includes in said first region a filter chamber hermetically sealed relative to the environment for collecting desublimated and/or sedimented salt and/or sedimented metal oxide, said gas outlet opening into said filter chamber, and said apparatus further comprises a gas line connecting the filter chamber with said condensing unit in such a way that the gas stream can flow via the filter chamber after passing the filter means through the gas line into the condensing unit.

15. The apparatus as claimed in claim 14, further comprising:

connecting elements connecting said gas outlet and said heatable filter unit, said connecting elements being thermally insulated and/or equipped with heating elements in such a manner, that their temperature is settable to more than 100° C.

16. The apparatus as claimed in claim 1, further comprising:

an infrared measuring arrangement for determining a gaseous $CO_2$ content in said analysis chamber: and/or a chemiluminescence detector for determining a $NO_x$ content in said analysis chamber.

17. The apparatus as claimed in claim 14, further comprising:

an infrared measuring arrangement for determining a gaseous $CO_2$ content in said analysis chamber; and/or a chemiluminescence detector for determining a $NO_x$ content in said analysis chamber.

18. An apparatus for determining the content of at least one oxidizable constituent of an aqueous, liquid sample, comprising:

an analysis chamber;

a high temperature reactor for decomposing the liquid sample and forming a gaseous mixture, which contains at least the constituent as a gaseous oxide, said high temperature reactor settable to a reactor temperature and having a liquid inlet for delivery of the liquid sample, a gas inlet for delivery of a carrier gas, and a gas outlet;

a condensing unit for condensing water from the gas mixture;

a heatable filter unit for removal of salts and/or metal oxides from the gas mixture, the filter unit arranged separate from the high temperature reactor such that the filter unit is settable to a filter temperature substantially below the reactor temperature, the apparatus structured to be operated such that a gas stream of the carrier gas and the gas mixture of said high temperature reactor passes from said gas outlet via said heatable filter unit to said condensing unit and into said analysis chamber, the condensing unit being placed in the direction of the gas stream in front of said analysis chamber; and an infrared measuring arrangement for determining a gaseous $CO_2$ content in said analysis chamber and/or a chemiluminescence detector for determining a $NO_x$ content in said analysis chamber, wherein said gas outlet and said heatable filter unit are connected by a gas line, and said gas outlet, said heatable filter unit and said gas line are thermally insulated and/or equipped with heating elements such that their temperature during operation of the apparatus is settable to a temperature less than the reactor temperature and between 100° C. and 150° C.

19. The apparatus according to claim 1, wherein:

said high temperature reactor comprises a pyrolysis tube, said pyrolysis tube including the gas outlet, which opens into the filter chamber of said filter unit so that a gas mixture produced in said pyrolysis tube can flow with the carrier gas via said gas outlet into said filter chamber.

20. The apparatus according to claim 19, wherein:

said filter chamber is connected with said condensing unit via a second gas line in such a way that a gas stream flowing from said gas outlet into the filter chamber can flow via the filter chamber through the second gas line into said condensing unit.

21. The apparatus according to claim 1, wherein said high temperature reactor comprises a reaction zone, which is heatable to a temperature between 680° C. and 1000° C. during operation of the apparatus.

22. The apparatus according to claim 18, wherein said high temperature reactor comprises a reaction zone which is heatable to a temperature between 680° C. and 1000° C. during operation of the apparatus.

\* \* \* \* \*